United States Patent [19]

Langer et al.

[11] Patent Number: 4,906,474
[45] Date of Patent: Mar. 6, 1990

[54] BIOERODIBLE POLYANHYDRIDES FOR CONTROLLED DRUG DELIVERY

[75] Inventors: Robert S. Langer, Somerville, Mass.; Howard Rosen, Montara, Calif.; Robert J. Linhardt, Iowa City, Iowa; Kam Leong, Cambridge, Mass.

[73] Assignee: Massachusetts Institute of Technology, Cambridge, Mass.

[21] Appl. No.: 613,001

[22] Filed: May 21, 1984

Related U.S. Application Data

[63] Continuation of Ser. No. 477,710, Mar. 22, 1983, abandoned.

[51] Int. Cl.$^4$ .............. A61M 31/00; A61F 7/02; A61F 5/46; C08G 63/02
[52] U.S. Cl. .................. 424/428; 528/271; 528/206; 528/207; 424/78; 424/409; 424/426; 424/466; 424/497; 604/891.1
[58] Field of Search .............. 524/17, 21, 599; 424/19, 78, 424, 426, 466, 428, 78, 497; 604/890, 891, 892, 897

[56] References Cited

U.S. PATENT DOCUMENTS

| | | | |
|---|---|---|---|
| 2,071,250 | 2/1937 | Carothers | 160/106 |
| 2,071,251 | 2/1937 | Carothers | 18/54 |
| 2,073,799 | 3/1937 | Hill | 260/112 |
| 2,668,162 | 2/1954 | Lowe | 260/78.3 |
| 2,676,945 | 4/1954 | Higgins | 260/45.7 |
| 2,958,678 | 11/1960 | Conix | 260/78.4 |
| 2,960,493 | 11/1960 | Conix | 260/47 |
| 3,526,612 | 9/1970 | Allphin | 260/78.4 |
| 3,625,214 | 12/1971 | Higuchi | 128/260 |
| 3,766,145 | 10/1973 | Thompson | 260/75 EP |
| 3,811,444 | 5/1974 | Heller et al. | 128/260 |
| 3,914,401 | 10/1975 | Sharabash | 424/19 |
| 3,960,150 | 6/1976 | Hussain et al. | 128/260 |
| 3,976,071 | 8/1976 | Sadek | 128/260 |
| 3,981,303 | 9/1976 | Higuchi et al. | 424/428 |
| 3,986,510 | 10/1976 | Higuchi et al. | 424/428 |
| 3,993,071 | 11/1976 | Higuchi et al. | 424/428 |
| 4,014,987 | 3/1977 | Heller et al. | 424/15 |
| 4,036,227 | 7/1977 | Zaffaroni et al. | 128/260 |
| 4,070,347 | 1/1978 | Schmitt | 260/77.5 D |
| 4,096,238 | 6/1978 | Zaffaroni et al. | 424/15 |
| 4,489,056 | 12/1984 | Himmelstein et al. | 424/22 |

FOREIGN PATENT DOCUMENTS

| | | | |
|---|---|---|---|
| 684685 | 4/1964 | Canada | 427/428 |
| 2590262 | 5/1987 | France | 427/428 |
| 60-141725 | 7/1985 | Japan | 424/428 |
| 838986 | 6/1960 | United Kingdom | 427/428 |
| 840846 | 7/1960 | United Kingdom | 428/428 |
| 840846 | 7/1960 | United Kingdom | . |
| 840847 | 7/1960 | United Kingdom | 427/428 |
| 968715 | 9/1964 | United Kingdom | 427/428 |

OTHER PUBLICATIONS

Rosen, H. B. et al. (including J. Chang and G. E. Whek) Biomaterials, Apr. 83, vol. 4, No. 2, pp. 131-133 "Bioerodible Polyanhydrides for Controlled Drug Delivery."
Rosen MIT Thesis dated Jan. 14, 1982, "Synthesis and Characterization of Bioerodible Polymers for Controlled Drug Release".
Rosen et al., *Biomaterials*, vol. 4, Apr. 1983, pp. 131-133, "Bioerodible Polyanhydrides for Controlled Drug Delivery".
Cottler et al., *Chemis Weckblud*, vol. 63 (1967).
"Synthesis of Polyanhydrides X. Mixed Anhydrides of Aromatic and Five-Membered Heterocyclic Dibasic Acids," by Naoya Yoda in *High Polymer Chem.*, Japan, 10-35 (1962).
"Bioerodible Polyanhydrides as Drug-Carrier Matrices, I: Characterization, Degradation, and Release Characteristics" by K. W. Leong, Brott, & Langer in *J. Biomed. Mtls. Res.*, 19,941-955 (1985).
"Bioerodible Polyanhydrides for Controlled Drug Delivery" by Rosen, Chang, Wnek, Linhardt, and Langer in *Biomaterials* 4, 131-133 (1983).
Synthesis of Polyanhydrides., XII., N. Yoda, *J. Polymer Sci.*, vol. 1, 1323-1338 (1963).
Synthesis of Polyanhydrides III., N. Yoda, 174-190 (1962), *Makromolekulare Chemi.* 55.
"Synthesis of Polyanhydrides: Melt-Polycondensation, Dehydrochlorination, and Dehydrative Coupling" *Macromolecules*, vol. 20, No. 4, 705-712 (Apr., 1987).
Bucher et al., *J. Amer. Chem. Soc.* 32, 1319 (1909).
Yoda, Makromolec. Chem. 36, (1962).
Yoda, *Makromolec. Chem.* 32, 1 (1959).
Yoda, *Makromolec. Chem.* 56, 10 (1962).
John E. Bucher and W. Clifton Slade, the Anhydrides of Isophthalic and Terephthalic Acids, *J. Amer. Chem. Soc.* 32, 1319 (1909).
Naoya Yoda, Synthesis of Polyanhydrides. XI., *Makromol. Chem.* 36 (1962).
Naoya Yoda, Syntheses of Polyanhydrides, XII. Crystalline and High Melting Polyamidepolyanhydride of Methylenebis (P-Carboxyphenyl)Amide, *Journal of Polymer Science*: Part A, vol. I, 1323 (1962).
Naoya Yoda, Synthesis of Polyanhydrides. II. New Aromatic Polyanhydrides with High Melting Points and Fiber-Forming Properties, *Makromol. Chem.* 32, 1 (1959).

(List continued on next page.)

Primary Examiner—Robin L. Teskin
Attorney, Agent, or Firm—Kilpatrick & Cody

[57] ABSTRACT

A composition of matter suitable for implantation in the body to effect zero order drug release comprising a drug and a polymer of the formula:

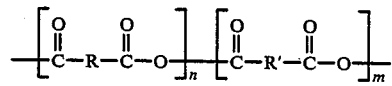

wherein R and R' can be the same or different and are hydrophobic organic linkages and n and m are integers of 1 or greater.

4 Claims, No Drawings

OTHER PUBLICATIONS

Naoya Yoda, Synthesis of Polyanhydrides. X. Mixed Anhydrides of Aromatic and Five-Membered Heterocyclic Dibasic Acids, *Makromol. Chem.* (1962).

Naoya Yoda and Akihisa Miyake, Synthesis of Polyanhydride. I. Mixed Anhydride of Aromatic and Aliphatic Dibasic Acids, *Makromol. Chem.* 32 (10), 1120 (1959).

Julian W. Hill and Wallace H. Carothers, Studies of Polymerization and Ring Formation. XIX. Many-Membered Cyclic Anhydrides, *J. Amer. Chem. Soc.* 55, 5023 (1933).

A. Conix, Poly[1,3-bis(p-Carboxyphenoxy)-Propane Anhydride], Macromolecular Syntheses, vol. two, 95 (1966).

Julian W. Hill and Wallace H. Carothers, Studies of Polymerization and Ring Formation. XIV. a Linear Superpolyanhydride and a Cyclic Dimeric Anhydride from Sebacic Acid, *J. Amer. Chem. Soc.* 54, 1569 (1932).

Polyanhydrides, *Ency. of Poly. Sci. & Tech.* 10, 630 (1969).

K. W. Leong, B. C. Brott and R. Langer, "Bioerodible Polyanhydrides as Drug-Carrier Matrices. I: Characterization, Degradation, and Release Characteristics,'-'*Journal of Biomedical Materials* Research 19, 941 (1985).

K. W. Leong, P. D'Amore, M. Marletta and R. Langer, "Bioerodible Polyanhydrides as Drug-Carrier Matrices, II., Biocompatibility and Chemical Reactivity," *Journal of Biomedical Materials* Research 20, 51 (1986).

BIOERODIBLE POLYANHYDRIDES FOR CONTROLLED DRUG DELIVERY

The invention described herein was made with support from a grant or an award from the National Institute of Health, GM 26698.

This application is a continuation of application Ser. No. 477,710, filed Mar. 22, 1983, now abandoned.

BACKGROUND OF THE INVENTION

In recent years, much research has been done in developing systems using polymeric compositions with a programed release of active agents, especially drugs, over periods of times. The purpose of these systems is to dispense the agent at a controlled and, if desired, constant rate in order, as in the case of pharmaceutical agents or drugs, to improve therapy by presenting the drug in a most beneficial and reliable manner, with a minimum possibility of complications from the drug or from failure to comply with the therapeutic regime.

Although controlled release of drugs can be accomplished by several mechanisms, biodegradation of an insoluble polymer carrier to soluble monomer units offers the advantage of eliminating the need for surgical removal of the device. However, the development of controlled release systems using bio-erodible polymers has not advanced as quickly as the non-erodible systems and at present, no bio-erodible system has been approved by the Food and Drug Administration for clinical application. In addition, there have been very few bio-erodible polymers developed for biomedical use, and unfortunately very few of the polymers were designed initially with the intention of releasing drugs in a controlled manner. This design deficiency has caused difficulty in developing effective controlled release dosage forms from these polymers.

The ideal situation for an effective bio-erodible system is one where the drug is uniformly distributed through the polymer and where surface erosion is the only factor permitting drug release to occur in order to obtain advantageous cost and dosage form design. With an erosion rate constant, k, the rate of release dM/dt is equal to the product of k and the surface area of the system. Therefore, to obtain zero-order release, it would be necessary to utilize a geometry that does not change its surface area as a function of time. Such ideal systems would also possess the following additional advantages: (1) simple release mechanism which is independent of drug properties, (2) ability to linearly vary drug delivery rate by linerally varying the load of the device with a drug, (3) conservation of mechanical integrity since erosion occurs only at the surface of the device, (4) linearly vary device life by linearly varying device thickness and (5) elimination of the polymer and drug concomitantly.

However, the ideal situation described in which surface erosion is the only factor responsible for drug release and with the polymer degraded to small nontoxic products, has never been found in practical usage and this makes it difficult to achieve zero-order release and difficult to control release kinetics. Worse still, bulk erosion often occurs in addition to surface erosion rendering the system sponge-like which causes even greater difficulty in both controlling release because of multiple phenomena (including diffusion), taking place and accomplishing zero-order release.

The reason for the bulk erosion problem is that almost every bio-erodible polymer which has been developed for biomedical use such as polylactic acid has been hydrophilic and imbibes water into the center of the matrix. It is not surprising since most bio-erodible polymers developed for biomedical use where designed for use as suture materials rather than for controlled release application. In addition to polylactic acid, other hydrophilic polymers have been studied including polyglutamic acid, polycaprolactone and lactic/glycolic acid copolymers. However, while these systems may be useful under certain circumstances, they still possess the above-mentioned limitations.

The only bio-erodible hydrophobic polymer which has been designed for drug delivery systems are polyorthoesters. They have advantages in that they are not only hydrophobic, but their hydrophobicity is pH-sensitive and this has proven useful in regulating drug release. However, although different types of polyorthoesters have been synthesized, they have been reported to possess certain disadvantages such as (1) by themselves, they are often too hydrolytically stable for controlled drug release, e.g. 7% by weight erodes in over 220 days. They therefore need the inclusion of acid catalysts to promote bio-erosion. (2) They also swell a great deal as a result of the incorporation of sodium carbonate into the matrix, the rate of swelling often contributes more to determining release rates than does the rate of erosion. Also, the degradation products are not as simple as some other bio-erodible polymers such as polylactic acid which has the advantage that the ultimate degradation products are water and carbon dioxide.

It would be highly desirable to provide a hydrophobic bio-erodible polymer system for controlling drug release wherein the erosion intermediates and products are nontoxic and are readily eliminated or metabolized by the body. In addition, it would be desirable to provide such a polymer system which does not cause adverse tissue reaction. In addition, it would be desirable to provide such a system that exhibits mechanical and physical integrity, is unswellable, is tight enough to prevent diffusion, is easy to synthesize and form and is stable on storage.

SUMMARY OF THE INVENTION

In accordance with this invention, polyanhydrides of the formula

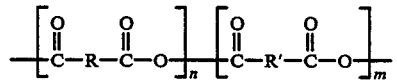

wherein R and R' can be identical or different, and can be any one of a wide variety of hydrophobic molecular linking units are admixed with a drug and the resultant mixture is formed to form a drug delivery system. The drug delivery system then can be implanted in the environment of use such as subcutaneously in the human body. It has been found that the polyanhydride matrix erodes heterogeneously from the surface first so that the erosion leads to zero-order of drug release and the overall shape of the drug delivery system remains nearly constant.

DESCRIPTION OF SPECIFIC EMBODIMENTS

The polymer matrices utilized in the present invention are those having the formula:

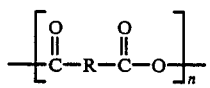

wherein R or R' is a linking moiety having hydrophobicity such as allyl group bearing from 1 to 20 carbon atoms, a backbone having aromatic moieties such as p-carboxyphenoxy methane, benzyl substituted or unsubstituted benzenes or pyridine or other heterocyclic aromatic of the like [The homopolymer (R=R') and the copolymer (R≠R') can have an average degree of polymerization ranging from 10 to 106. The monomers in the copolymer can be distributed regularly or at random]. Since the anhydride linkage is highly reactive toward hydrolysis, it is preferable that the polymer backbone be hydrophobic in order to attain the heterogeneous erosion of the composition, thereby to obtain the zero-order drug release. Hydrophobicity can be regulated easily, for example by regulating the concentration of aromatic moieties in the linking backbone, or by monitoring the monomer ratio in the copolymer.

A particularly suitable backbone comprises the product of an aliphatic dicarboxylic acid and an aromatic amino acid such as 1-phenylalanine, tryptophan, tyrosine or glycine.

Any biologically active substance can be utilized in conjunction with the polyanhydride so long as it is capable of being intimately admixed with the polyanhydride and subsequently formed into a desired shape without affecting the bioavailability of the drug. The active substance can be a protein or it can be nonproteinaceous; it can be a macromolecule (M.W.>2/1000 daltons) or a smaller molecule; and it can be soluble or insoluble in water. Examples of suitable active substances are interferon, anti-angiogenesis factors, antibodies, antigens, polysaccharides, growth factors, hormones including insulin, glucogen, parathyroid and pituitary hormones, calcitonin, vasopressin, renin, prolactin, growth hormones, thyroid stimulating hormone, corticotrophin, follicle stimulating hormone, luteinizing hormone, and chorionic gonadotropins; enzymes, including soybean trypsin inhibitor, lysozyme, catalase, tumor angiogenesis factor, cartilage factor, transferases, hydrolases, lysases, isomerases, proteases, ligases and oxidoreductases such as esterases, phosphatases, glycosidases, and peptidases; enzyme inhibitors such as leupeptin, antipain, chymostatin and pepstatin; and drugs such as steroids, anti-cancer drugs or antibiotics.

A laminar matrix consisting of layers of polymer with different levels of drug loading can also be fabricated to yield a programed release pattern, provided that diffusion of the bioactive molecules within the matrix is negligible compared to degradation of the polymer device.

The relative proportions of the biologically active molecule incorporated into the polyanhydride matrix to form the two phase system can be modified over a wide range depending upon the molecule to be administered and the desired effect. Generally, the molecule can be present in an amount which will be released over controlled periods of time, according to predetermined desired rates, which rates are dependent upon the initial concentration of the active molecule in the matrix. This necessarily implies a quantity of molecule greater than the standard single dosage. Proportions suitable for the purpose of this invention can range from about 1 to 50 parts by weight of biologically active molecule to between about 99 and about 50 parts by weight of polyanhydride matrix, preferably between about 10 and about 30 parts by weight of biologically active molecule formulated with sufficient polyanhydride matrix to give 100 parts by weight of a final system.

The polyanhydride matrix and the biologically active molecule can be admixed intimately in any convenient manner, preferably by mixing the components as powders and subsequently forming the mixture into a desired shape such as by thermal forming at a temperature less than that which the biologically active molecule will become degraded, and at which the polymer has desirable morphological properties. Generally, the final composition is formed as a slag which can be circular, rectangular or the like and having a thickness between about 1 mm and about 100 mm and a total surface area between about 0.01 cm$^2$ and about 1000 cm$^2$ preferably between about 1 cm$^2$ and about 100 cm$^2$. It has been found that when the polyanhydride-biologically active molecule mixture is formed into this relatively thin shape, zero-order release of the biologically active molecule can be more easily attained. The delivery systems of this invention can be manufactured as devices that can take a wide range of shapes, sizes and forms for delivering the biologically active molecule to different environments of use. For example, the systems can be made as devices including buccal and oral devices; vaginal and intrauterine devices of slendrical, bullet, elliptical, circular, bulbous, loo, bow or any other shape that lends itself to placement in these biological environments; the devices also include ocular devices of any geometric shape for comfortable placement in the cul de sac such as ellipsoid, bean, banana, circular, rectangular, doughnut, crescent and half-ring shaped devices. In cross section, the ocular devices can be doubly convex, concavo-convex and the like. The dimensions of the ocular devices can vary according to the size of the eye, with satisfactory eye devices generally having a length of 4-20 mm or width of 1-15 mm and a thickness of 0.1-4 mm. Other devices made according to this invention include implants, anal, pessaries and prosthetic devices, artificial glands for dispensing a pharmaceutically active molecular agent having a physiological function essentially equivalent to a corresponding natural gland, cervical, nasal, ear and skin devices.

The systems of this invention with the systems designed in the form of devices are manufactured by standard techniques provided as is important to this invention that such manufacture include process steps such as blending, mixing or the equivalent thereof for structurally defining the system comprising the biologically active molecule and the polyanhydride matrix forming material.

For example, one suitable method for making the systems comprises dissolving the polyanhydride in an appropriate solvent, therefore to form a casting solution, mixing a known amount of the biologically active molecule in the casting solution, charging the solution into a mold and then drying the mold, usually under vacuum, causing the polyanhydride to precipitate and form the matrix with the biologically active molecule phase therein. Alternatively, the polyanhydride in the form of a powder can be admixed with the biologically active molecule in the form of a powder and then molded under adequate temperature and pressure to the desired shape, through injection, compression or extrusion.

The following examples illustrate the present invention and are not intended to limit the same.

EXAMPLE I

Poly[bis(p-carboxyphenoxy)methane] (PCPM), was chosen as a prototype to examine the usefulness of polyanhydrides in controlled release devices. PCPM, synthesized by an adaption of the method of Conix, J. Polym. Sci., 29, 343-353 (1958) and Macromolecular Synthesis, Vol 2., J. R. Elliot, ed., NYC, 95-99 (1966), was a yellow translucent amorphous solid with a $Tg=92°$ C. (5° C. higher than reported by Conix and no observable Tm (a sample with cholic acid incorporated did, however, show a $Tm=192°$ C. due to cholic acid melting). The polymer had carbonyl stretching frequencies in the infrared of 1770 and 1720 cm.

To formulate drug-free matrices, PCPM was ground using a Fisher Scientific Micro Mill and the resulting particles sized using sieves. PCPM particles (150-300 um diameter) were melt pressed between sheets of aluminum foil at temperatures and pressures ranging from 93° C. to 163° C. and 22 kpa to 81 kpa on a Carver Laboratory press, using shims to regulate device thickness. At temperatures below 120° C., the polymer did not flow well giving devices with poor mechanical properties. At temperatures above 145° C., the devices formed were brittle. There were no discernible differences between devices pressed over the range of 22 to 81 kpsi. The conditions chosen to melt press PCPM were 121° C. and 22 kpsi giving devices with suitable mechanical properties and minimizing the possible induction of morphological changes within the polymer during pressing. PCPM hydrolyzed completely leaving no insoluble residue. The UV spectra of the erosion product was identical to that of the diacid monomer bis(p-carboxyphenoxy)methane.

The matrix dimensions examined ranged from having face areas of 0.2 to 0.8 $cm^2$ and having thicknesses of 0.05 to 0.10 cm.

To incorporate a drug, unlabelled cholic acid from Sigma Chemical Co. (15 mg) was dissolved in 10 ml of ethanol. Tritiated cholic acid (2.4-3H) from New England Nuclear, in 125 ul of ethanol ($2.42 \times 10^8$ DPM, S.A.=$3.72 \times 10^{10}$ DPM/mg) was added to the unlabelled solution and the solution was dried in vacuo. The drug powder (10.5 wt %) was mixed with the PCPM particles and melt-pressed as above. The drug containing device was then sandwiched between two very thin (<1 wt %) drug free layers of ground (150-300 um diameter) PCPM to eliminate the presence of surface exposed drug particles and then repressed.

In vitro erosion and drug release studies were performed by placing the PCPM devices weighing from 10-50 mg in glass scintillation vials containing 10 ml of 0.2M phosphate buffer (pH 7.4) at 37° or 60° C. The buffer was periodically changed by removing the device from the vial and placing it in a vial of fresh buffer. The absorbance of the collected buffer solutions was measured on a Gilford spectrophotometer at 243 nm to detect the diacid monomer, bis(p-carboxyphenoxy)methane. Concentrations from 0 to 0.02 mg/ml. The polymer devices containing tritiated cholic acid were eroded and the buffer solutions were analyzed on a LS-230 Beckman scintillation counter.

In vivo erosion was studied using three portions cut from a single melt-pressed PCPM slab each with the dimensions 0.26 $cm^2$ face area $\times$ 0.0695 cm thick and weighing 24 mg. The squares were sterilized under UV light for 30 mins. Each square was implanted subcutaneously in the abdominal region ofd a Sprague-Dawley rat. An animal was sacrificed at the end of 21, 44 and 153 days and the polymer removed, dried and weighed.

The erosion curves for drug-free PCPM slabs at both 37° C. and 60° C. are shown in FIGS. 1 and 2. Both curves are characterized by an induction period followed by a linear region of mass loss at a constant rate. Throughout the erosion, the devices decreased in size while maintaining their physical integrity suggesting surface erosion.

The erosion profile was unaltered by scraping the polymer matrix to remove surface layer; the same induction period was observed. When polymer matrices were pre-eroded for 50 hours at 60° C. (until the induction period ended), removed, vacuum dried, and returned to fresh buffer solutions at either 37° C. or 60° C., zero-order erosion of the samples began, almost immediately (FIGS. 3 and 4).

Drug release from PCPM was investigated in vitro using cholic acid which, because of its low UV absorbance at 243 nm did not interfere with matrix erosion measurement. The erosion and release profiles were nearly zero-order and had similar slopes (FIG. 5).

The in vivo erosion of drug-free PCPM slabs showed a half-life of about 47 days or approximately 5 days shorter than in vitro erosion at 37° C. in pH 7.4 buffer. After 153 days, <1% of the polymer remained. The devices were only slightly encapsulated by tissue.

These studies using PCPM as a prototype polyanhydride show the suitability of this polymer class for use in bioerodible drug delivery systems. PCPM completely degrades to its monomer, under physiological conditions at rates useful for drug delivery applications. The erosion profile (FIGS. 1 and 2) is characterized by an induction period followed by a period of linear zero-order erosion. An investigation of this induction period was conducted by scraping the surface layers from the polymer matrix. The fact that such treatment did not eliminate or shorten the induction period indicates that morphological surface changes, occurring during the melt pressing, are not the cause of this induction period. The induction period was, however, eliminated by pre-eroding followed by vacuum drying the device. The effectiveness of this pretreatment step shows that 2 rate constants control the rate of device erosion. The first is the rate of hydrolysis of the anhydride linkage and the second the rate of polymer dissolution. In order to begin to measure monomer units in the buffer, it is likely that many anhydride linkages on the polymer's surface must be cleaved. This non-productive hydrolysis corresponds to the observed induction time. Pre-erosion of the device presumably decreases the surface polymers' chain length and in the subsequent erosion, the anhydride hydrolysis rate and device dissolution rate become equivalent.

The decrease in the device thickness throughout the erosion and the maintenance of the matrices structural integrity as well as the zero-order erosion kinetics shows that heterogeneous surface erosion predominants. PCPM eroded in vivo slightly faster than its in vitro erosion in phosphate buffer at pH 7.4 at the same temperature. The thin, partially eroded, polymer slabs were difficult to completely remove from the rats and hence may be the cause for the slightly accelerated in vivo erosion rate measurement. No tissue irritation was apparent and only slight device encapsulation occurred within the test animals.

FIGS. 1 AND 2

Erosion curves for drug-free PCPM matrices in phosphate buffer at 37° C. (a) and 60° C. (b). Percent polymer eroded is 100×the cumulative mass eroded at each sample point divided by the total mass of the matrix. The matrices tested at 37° and 60° C. weighed 23 and 18 mg respectively.

The PCPM matrices eroded at 37° C. and 60° C. were pressed in the same rectangular mold and had the dimensions 0.24 cm$^2$ face area×0.08 cm thick and 0.33 cm$^2$ face area×0.05 cm thick respectively.

FIGS. 3 AND 4

Erosion curves for the drug-free PCPM matrices which have been pre-eroded at 60° C. for 50 hours. Erosion took place in phosphate buffer at 37° C. (a) and 60° C. (b). Percent polymer erosion is 100×the cumulative mass eroded at each sample point divided by the total mass of the matrix. The matrices tested at 37° and 60° C. weighed 74 and 25 mg respectively. The PCPM matrices eroded at 37° C. and 60° C. had the dimensions 0.57 cm$^2$ face areas×0.06 cm thick and 1.13 cm$^2$ face area×0.05 cm thick respectively.

FIG. 5

Erosion and release curves for a PCPM matrix containing cholic acid at 10.5 wt % eroded in phosphate buffer at 60° C. PCPM erosion is plotted as percent polymer erosion which equals 100×the cumulative mass eroded at each sample point divided by total mass of the matrix 25 mg. Cholic acid release is plotted as the percent cholic acid released which equals 100×the cumulative counts per minute at each sample point divided by the total number of counts per minute within the polymer. The matrix has the dimensions 0.5 cm$^2$ face area×0.06 cm thick.

EXAMPLE II

To further demonstrate the applicability of polyanhydrides as drug carrier matrix, the higher homolog of PCPM, poly[bis(p-carboxyphenoxy)propane] (PCPP) (Equation 2), was synthesized and its degradation characteristics studied.

PCPP was similarly synthesized by adopting the method described by Conix. The polymer appeared dark brown as a result of contamination and decomposition during polymerization at high temperature. To obtain a colorless product, the prepolymer was repeatedly recrystallized in acetic anhydride until a snowy white prepolymer was obtained. Immersed in a parafin oil bath, the polymerization tube containing the prepolymer was swept by dried nitrogen under a dynamic vacuum of 10$^{-3}$ torr. The temperature of the oil bath was slowly raised to where the prepolymer just began to melt. Polymer thus obtained was only slightly yellow, and crystalline.

As determined by gel permeation chromatography and solution viscometry, the polymer had a weight average molecular weight of 15,000 and a polydispersity of 3.6. The low molecular weight species dissolved in THF, DMF, and other polar solvents, while the higher molecular weight polymer dissolved well only in phenol. The Tg and Tm obtained from DSC measurements were 75° and 240° respectively.

PCPP, after being ground, was compression molded into thin slabs at 150° C. and 50 Kpsi. The in vitro erosion rate of the polymer was approximately 5 times lower than that of PCPM in 7.4 pH phosphate buffer at 37° C. Erosion rate increased with pH. The device maintained its physical integrity except at pH higher than 9 where some small particles separated from the matrix. At pH 1, the erosion rate was almost negligible. Such a pH-sensitivity might prove advantageous in certain applications.

Preliminary toxicological tests indicated that the polymer was biocompatible. Both the monomer and the polymer extract in physiological saline exhibited neither mutagenicity nor carcinogenicity as tested by a forward mutation assay in Salmonella typhimurium based on resistance to the purine analog δ-azaguanine.

EXAMPLE III

A different approach to regulate the matrix erosion rate is to synthesize a copolyanhydride having monomers of different hydrophobicities. The copolymer chosen for study was poly(terephthalic acid-sebacic acid) (Equation 3). While poly(sebacic acid) hydrolytically degrades in atomospheric moisture, the hydrophobic and crystalline poly(terephthalic acid) is highly resistant to hydrolysis. The two monomers hence present the two extremes of hydrophobicity and crystallinity. By varying the terephthalic acid to sebacic acid ratio in the copolymer, a carrier matrix with a spectrum of degradation rates can then be obtained. Additionally, the elastic property of the matrix can be fine tuned from rigid to rubbery.

The copolymer was synthesized by reaction desired proportions of terephthalic acid and sebacic acid with acetic anhydride. The resulting mixed anhydrides underwent thermal polycondensation in vacuo to yield a randomly distributed block copolymer.

Copolymers with terephthalic acid concentrations of 0, 30, 50, 80 and 100 percent had been obtained. They were compression molded into thin slabs and placed in buffer solutions for erosion kinetics study. The erosion rate was indeed inversely proportional to the concentration of terephthalic acid. The extract of the copolymer in physiological saline was also non-mutagenic and non-carcinogenic as determined by the forward mutation assay in *Salmonella typhimurium*.

The examples given above clearly illustrated the potential of polyanhydrides as biodegradable carrier matrix. Over 100 homo or copolyanhydrides had been synthesized as reviewed by R. J. Cottler and M. Matzner, Chemis Weekblad, 63 (1967), p. 113. Many more new ones can be synthesized according to the general reaction scheme of converting a dicarboxylic acid to a mixed anhydride (Equation 4), and through thermal polycondensation of the mixed anhydride into the polymer (Equation 5).

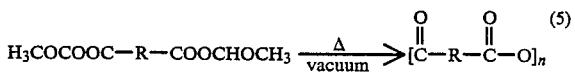

Choice of the functional group R. is dictated by the desired effects and is discussed below.

As mentioned above, in conclusion of polar groups such as phenylene along the backbone or as pendant increases the hydrophobicity and hence reduces the degradation rate of polyanhydride. In addition, groups that enhance intramolecular interaction by hydrogen bonding or van der waal forces, such as an amide linkage in the back one, would produce similar effect.

Another important factor crystallinity which resists penetration of water into the polymer matrix. A symmetric functional group promotes regular atomic arrangement and hence crystallinity. Substitution of the aromatic hydrogen by a bulky group would prevent close packing as a result of steric hindrance and tend to increase the erosion rate. Functional groups such as hydroxyl and amide, however, should not be used because of their reactivities toward the carboxyl group and would induce crosslinking during polymerization.

Groups that have strong resonance interaction with the carbonyl group would stabilize the anhydride linkage toward hydrolysis. Electron rich groups such as a phenylene nucleus neighboring to the carbonyl group for that reason will render the polymer more stable because of the possible $\pi-\pi$ orbital overlap.

For toxicological reasons, phenylene group is best placed in the backbone of the polymer chain to minimize epoxide formation. Halogens, nitro, and cyano groups or the like are to be avoided.

EXAMPLE IV

This example illustrates the preparation of novel polyanhydrides useful in the present invention.

(1) Two Amino Acids per Monomer: The monomer is synthesized by connecting the amino groups of two molecules of L-phenylalanine or any other suitable amino acid, through a peptide linkage to an aliphatic diacid (shown below).

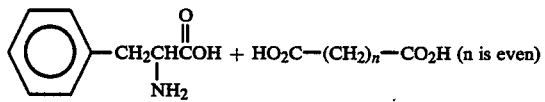

L-PHENYLALANINE  ALIPHATIC DIACID

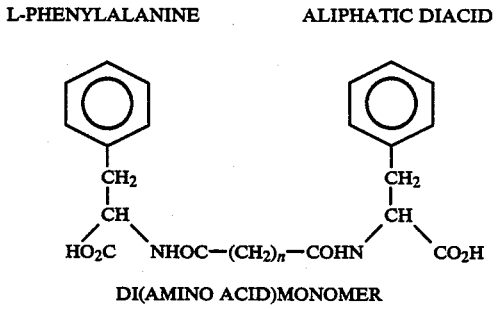

DI(AMINO ACID)MONOMER

Succinic acid or other naturally occurring diacids are used. L-amino acids are used because they are also naturally occurring. The phenyl groups on the amino acid would provide the required hydrophobicity. Also, the length of the aliphatic acid can be used to affect hydrophobicity and hence bioerosion rates. Bioerosion rate can also be varied by using different combinations of amino acids. One advantage of this monomer is its symmetry since this promotes crystallinity which helps prevent water absorption as discussed above.

(2) Amino Diacid Monomers: The monomer is based on three naturally occurring amino diacids: L-aspartic acid, L-glutamic acid and L-α-aminoadipic acid. For the small amounts of amino acids being degraded in controlled release implants, it is unlikely that any toxicity would occur.

L-ASPARTIC ACID  L-GLUTAMIC ACID

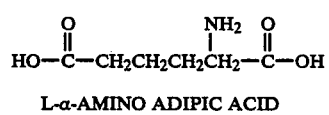

L-α-AMINO ADIPIC ACID

The amino group on the amino acid must be blocked to prevent polypeptide formation during polymerization. However, the choice of blocking agent provides a convenient way to control polymer hydrophobicity and crystallinity. The blocking groups to be used are naturally occurring saturated fatty acids of differing lengths (to control hydrophobicity) or benzoic acid.

BENZOIC ACID  SATURATED FATTY ACIDS

As discussed above, the hydrophobicity and crystallinity will regulate erosion rate. These properties may also vary depending on which of the three amino acids are employed.

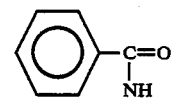

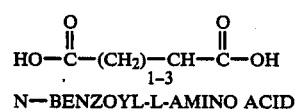

N—BENZOYL-L-AMINO ACID

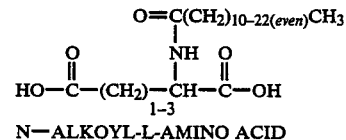

N—ALKOYL-L-AMINO ACID

The monomers shown above are a combination of two naturally occurring molecules and it is unlikely that they are toxic as they can be eliminated directly by the body. Alternatively, the peptide linkage can be hydrolytically or enzymatically (by a non-specific protease) cleaved to yield the amino acid and benzoic or saturated fatty acid.

SYNTHESIS OF POLY(N-BENZOYL-L-GLUTAMIC ACID)

(1) Introduction: The synthesis of Poly(N-benzoyl-L-glutamic acid) (PBGA) requires three steps: (i) blocking the amino group; (ii) forming the mixed anhydrides of N-benzoyl-L-glutamic acid (BGA) and acetic acid: and (iii) polymerization. These three steps are used in any class of polyanhydrides.

(2) Synthesis of Mixed Anhydride Prepolymer: The mixed anhydride of BGA and acetic acid is a prepolymer for the polymerization step. It is prepared by the method of Conix which was used in the prototype synthesis of PCPM.

In a trial run, BGA (200 mg) was refluxed in excess acetic anhydride (10 ml) at 152° C. for 5½ hours. BGA dissolved quickly in the warm acetic anhydride to form a clear solution. The reaction mixture turned yellow and then brownish yellow as the reaction proceeded. A brownish solid was recovered by reducing the reaction mixture to an oil and adding petroleum ether. The yield was 50% of theoretical.

An IR spectra of the mixed anhydride would be expected to show a characteristic carbonyl doublet for the anhydride at 1820 cm$^{-1}$ and 1760 cm$^{-1}$. A characteristic band should also be present at 1650 cm$^{-1}$ due to the amide carbonyl. An IR spectra of the brownish solid prepolymer showed bands at 1830 cm$^{-1}$, 1750 cm$^{-1}$ and 1650 cm$^{-1}$. Therefore, the agreement between the predicted spectra and the actual spectra of the brownish solid prepolymer and the absence of the band associates with the hydroxyl group positively identified the solid material as the mixed anhydride.

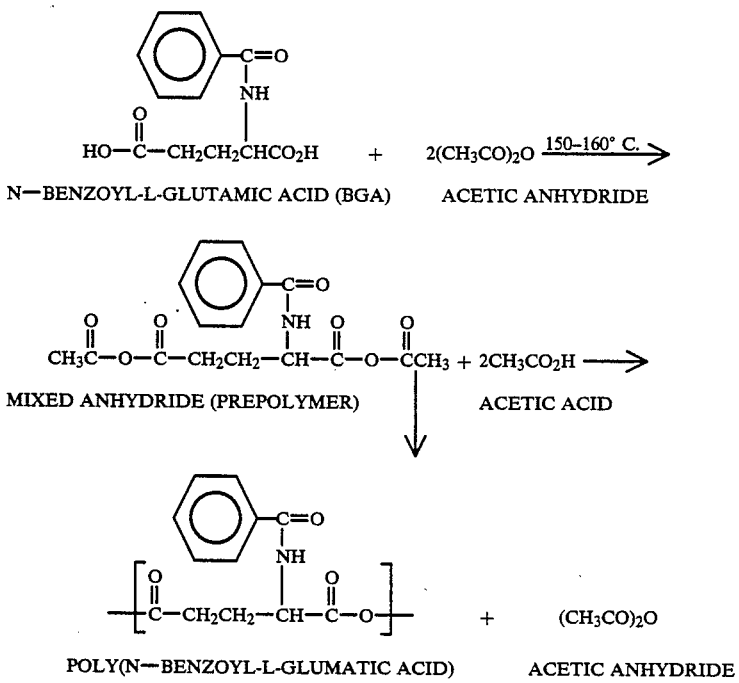

Two other general procedures exist for synthesizing anhydrides which may be adaptable to preparing BGA, acetic acid mixed anhydrides. Both procedures used stoichiometric quantities of reactants so dimer and cyclic anhydride formation should be reduced.

The first of these procedures involves the addition of acetyl chloride to pyridine in benzene with stirring. To this mixture, BGA would be added resulting in the formation of prepolymer. This procedure is an adaptation of the preparation of heptanoic anhydride from heptanoic acid and heptanoyl chloride.

The second procedure involves adding acetyl chloride dropwise to a stirred suspension of the disodium salt of BGA suspended in benzene. After the reaction is complete the mixture would be filtered and concentrated. This method has been used to prepare phenylacetic anhydride from phenylacetylchloride and sodium phenylacetate.

We claim:

1. A composition of matter comprising a mixture of a therapeutic drug and a polymer of the formula:

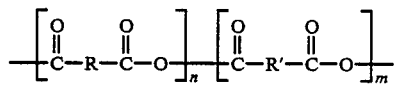

wherein R and R' can be the same or different and are hydrophobic organic linkages, the sum of n and m is between 10 and 106, and said polymer is polymerized from prepolymers formed from dicarboxylic acids, wherein the prepolymers are purified by recrystallization until the contaminants and degradation products present in the prepolymer are removed, said polymer being characterized by biocompatibility that results in minimal tissue irritation when implanted in vasculated tissue, and approximately zero order erosion and release rates of drug in vivo as a function of hydrolysis of the anhydride linkages in the polyanhydride.

2. The composition of claim 1 wherein R and R' are selected from the group consisting of an alkyl from 1 to 20 carbon atoms, p-carboxyphenoxymethane, benzyl, pyridine, and aromatic amino acids.

3. The composition of claim 2 wherein the amino acid is selected from the group consisting of phenylanine, tyrosine, tryptophan, and glycine.

4. The composition of claim 1 wherein the drug is selected from the group consisting of biologically active proteins, steroids, and antibiotics.

* * * * *